United States Patent [19]

Weston

[11] Patent Number: 5,370,317
[45] Date of Patent: Dec. 6, 1994

[54] ATOMIZING DEVICE FOR PRODUCING A SPRAY FROM A LIQUID UNDER PRESSURE

[75] Inventor: Terence E. Weston, Stradbroke, Eye, England

[73] Assignee: Glaxo Group Limited, Greenford, United Kingdom

[21] Appl. No.: 180,526

[22] Filed: Jan. 12, 1994

Related U.S. Application Data

[63] Continuation of Ser. No. 907,916, Jun. 26, 1992, abandoned.

[30] Foreign Application Priority Data

Jun. 28, 1991 [GB] United Kingdom ............. 9114080.6
Mar. 18, 1992 [GB] United Kingdom ............. 9205969.0

[51] Int. Cl.$^5$ .............................................. B05B 1/32
[52] U.S. Cl. .......................... 239/533.14; 239/533.13;
239/533.15; 239/DIG. 12; 239/321; 239/506;
222/494; 222/496
[58] Field of Search ............... 239/320, 321, 340, 349,
239/350, 353, 354, 452–454, 456, 506, 533.1,
533.15, 570, DIG. 12, 533.13, 533.14; 222/494,
496

[56] References Cited

U.S. PATENT DOCUMENTS

| | | |
|---|---|---|
| 525,507 | 9/1894 | Neumeyer ............................ 239/452 |
| 1,589,245 | 6/1926 | Scott . |
| 2,144,874 | 1/1939 | Edwards . |
| 2,308,476 | 1/1943 | Gerrer ............................ 239/533.14 |
| 2,434,875 | 1/1948 | Turnbull et al. . |
| 2,555,803 | 6/1951 | Mashinter et al. . |
| 2,756,106 | 7/1956 | Schenk ............................ 239/453 |
| 2,768,860 | 10/1956 | Miller . |
| 2,805,891 | 9/1957 | Sanborn ............................ 222/494 |
| 3,471,065 | 10/1969 | Malone . |
| 3,545,682 | 12/1970 | Beard ............................ 239/DIG. 12 |
| 3,602,407 | 8/1971 | Grothoff ............................ 222/494 |
| 3,744,722 | 7/1973 | Burns . |
| 3,762,409 | 10/1973 | Lester . |
| 3,794,247 | 2/1974 | Corsette ............................ 239/327 |
| 4,117,957 | 10/1978 | Duffey . |
| 4,230,242 | 10/1980 | Meshberg . |
| 4,260,082 | 4/1981 | Rooney et al. . |
| 4,344,744 | 8/1982 | Schuster et al. . |
| 4,352,462 | 10/1982 | Watanabe et al. ................... 239/452 |
| 4,368,850 | 1/1983 | Szekely . |
| 4,437,611 | 3/1984 | Gilroy ................................ 239/453 |
| 4,494,701 | 1/1985 | Hensley et al. . |
| 4,511,082 | 4/1985 | Ballik et al. ........................ 239/453 |
| 4,597,558 | 7/1986 | Hafner et al. . |
| 4,621,772 | 11/1986 | Blythe et al. . |
| 4,648,559 | 3/1987 | Fuller . |
| 4,662,567 | 5/1987 | Knapp . |
| 4,746,067 | 5/1988 | Svoboda . |
| 4,830,284 | 5/1989 | Maerte . |
| 4,895,279 | 1/1990 | Schultz . |
| 4,921,142 | 5/1990 | Graf et al. . |
| 5,002,230 | 3/1991 | Norskov et al. . |
| 5,002,231 | 3/1991 | Reiter et al. . |
| 5,053,170 | 10/1991 | Drahos . |
| 5,154,328 | 10/1992 | Gueret ............................... 222/494 |

FOREIGN PATENT DOCUMENTS

| | | |
|---|---|---|
| 692821 | 7/1967 | Belgium . |
| 9909 | 4/1980 | European Pat. Off. . |
| 77910 | 5/1983 | European Pat. Off. . |
| 134122 | 3/1985 | European Pat. Off. . |
| 261649 | 3/1988 | European Pat. Off. . |
| 352532 | 1/1990 | European Pat. Off. . |
| 380743 | 8/1990 | European Pat. Off. . |
| 412648 | 2/1991 | European Pat. Off. . |
| 446401 | 9/1991 | European Pat. Off. . |
| 471323 | 2/1992 | European Pat. Off. . |
| 909736 | 5/1946 | France . |
| 565999 | 12/1944 | United Kingdom . |
| 2156433 | 10/1985 | United Kingdom . |
| 2162594 | 2/1986 | United Kingdom . |
| 2169657 | 7/1986 | United Kingdom . |
| 2176267 | 12/1986 | United Kingdom . |
| 14468 | 10/1991 | WIPO . |
| 16993 | 11/1991 | WIPO . |

*Primary Examiner*—Karen B. Merritt
*Attorney, Agent, or Firm*—Darby & Darby

[57] ABSTRACT

A method and device are described for atomizing liquids, in which the liquid is forced through an annular gap formed between a spherical or conical surface and a circumambient hole in a plate, which components may be displaced relative to one another to control the flow of liquid through the gap. The size of the gap is controlled by a stop.

28 Claims, 10 Drawing Sheets

ATOMIZING DEVICE FOR PRODUCING A SPRAY FROM A LIQUID UNDER PRESSURE

This is a continuation of application Ser. No. 07/907,916, filed Jun. 26, 1992, now abandoned.

FIELD OF THE INVENTION

The invention relates to atomizing devices commonly used as, but not limited to, hand held sprayers such as so-called aerosols and pump type atomizers, intended for the application of liquid household, cosmetic and pharmaceutical products.

BACKGROUND OF THE INVENTION

Aerosol type sprayers are used throughout the world for dispensing a wide range of products, for example hair lacquer, furniture polish, cleaners, paint, insect killers and medicaments. Until recently, chlorofluorocarbons (CFC's) were the most common of the propellant gases used in aerosols because they are inert, miscible with a wide range of products, are easily liquefied under low pressures, give a substantially constant product flow-rate, and can produce sprays of droplets having mean diameters in the range of 3 to over 100 micrometers. However, in the 1970's it was confirmed that CFC's were probably responsible for depleting the Earth's protective ozone layer, and in 1987, most countries signed the Montreal Protocol to phase out the use of CFC's. Alternative propellants were then introduced—for example liquefied hydrocarbon gases such as butane, and carbon dioxide, which is dissolved in the product,—but these are flammable or otherwise harmful to the environment, or react with the product, and these propellant gases are gradually being phased out. There has been much development of aerosols powered by compressed gas (e.g. nitrogen, air), and manually operated pump atomizers, and for the majority of applications the performance of such sprayers is adequate.

The main drawback of these non-CFC sprayers is that the smallest sized droplet that can be produced is about 40 micrometers diameter, and despite considerable development of so-called mechanical breakup nozzles, the use of high pressure (circa 15 bars) pumps, and low viscosity/surface tension product formulations, 40 micrometers appears to be the lower limit achievable with prior art methods and devices.

There are aerosol generators used for research and hospital applications, such as ultrasonic nebulisers and spinning disc generators, but neither is suitable for portable, convenient atomisers.

It is also possible to force liquid at high pressure through a very small hole (5–10 micrometers diameter) to produce droplets of about 5 micrometers diameter, but these methods are unsuitable or uneconomic for large scale manufacture, mainly because of the difficulty in making very small holes in a suitable material, and, to prevent blockage of the hole, the need for exceptional cleanliness in the manufacture of the parts, together with ultrafiltration of the fluid to be sprayed.

For veterinary and some human vaccination applications, high pressure (125–500 bars) spring or gas operated pumps (so-called needle-less injectors) are in common use to inject a jet of drug through the skin ("intradermal injection") without the use of needles, and attachments are available to convert the jet to a spray for administering drugs to the nasal passages of large animals such as swine. However, the smallest droplet size obtainable is in the order of 40 micrometers, and the range of applications for these injectors is limited.

Compressed air atomizers such as air brushes and commercial paint sprayers consume large quantities of air, and to obtain droplets of 5 micrometers with water for example, a gas to liquid ratio of over 30,000:1 is required, which is impractical for convenient, portable sprayers.

Nevertheless, there are some applications that rely on a smaller droplet size for maximum efficacy: space sprays such as flying insect killers should contain droplets ideally in the range of 20–30 micrometers diameter to ensure a long flotation time in the air, and for metered dose inhalers (MDI's) used for treating certain respiratory disorders it is essential that the aerodynamic particle size should be less than 15 micrometers, preferably less than 5 micrometers, so that the droplets are able to penetrate and deposit in the tracheobronchial and alveolar regions of the lung. For a spray composed of droplets with a range of sizes, more than 5% by weight of the droplets should have an aerodynamic size less than 6.4 micrometers, preferably more than 20 by weight of the particles have an aerodynamic size less than 6.4 micrometers.

Inhalers may also be designed to deliver drugs to the alveolar sacs of the lung to provide a route for adsorption into the blood stream of drugs that are poorly adsorbed from the alimentary tract. To reach the alveoli it is essential that the aerodynamic size of the particles is less than 10 micrometers, preferably 0.5–5 micrometers.

Many of the drugs used in the treatment of respiratory disorders are insoluble in vehicles such as water and are dispensed as suspensions. The drugs are produced in a respirable size of 1–5 micrometers. Particles of this size tend to block the very small holes (5–10 micrometers) used by known devices to generate droplets of about 5 micrometers diameter.

SUMMARY OF THE INVENTION

The present invention aims to provide a design of atomizing nozzle which is capable, inter alia, of being used to give a nozzle which will produce a spray of droplets of a size suitable for inhalation, without the use of liquefied gas propellants. However, the present invention is believed to be capable of being used to give a nozzle which will produce a spray of droplets having a mean diameter anywhere in the range of from 0.5 to over 100 micrometers.

According to the present invention there is provided an atomizing nozzle for producing a spray of droplets from a liquid passing through the nozzle under pressure, which nozzle comprises means defining an orifice; a closure member for the orifice, the orifice-defining means and closure member being relatively movable with respect to one another between a first position in which the closure member cooperates with the orifice to close it and a second position in which the closure member is spaced from the orifice-defining means to define a gap therebetween; and a stop for limiting relative movement between the orifice-defining means and the closure member to ensure that the width of the gap cannot exceed that which will produce a fine spray.

Although the invention is intended mainly for metered dose inhalers and manually operated pumps, it may also be applied in other applications requiring small droplets, for example in certain industrial processes.

In one embodiment of the present invention the nozzle has a circular orifice which is sealingly closed by a ball urged by a spring. Under the action of liquid under pressure, the ball is displaced from the orifice by an amount determined by the stop, which may be fixed or adjustable, and the fluid flows through the gap thus formed and emerges as a thin circular sheet. As the sheet of liquid expands it becomes thinner, and the outer edge breaks into droplets, the diameters of which are determined by the size of the gap, the pressure of liquid, and the physical properties of the liquid. When the pressure in the liquid is reduced below a predetermined level, the ball is urged by the spring sealingly onto the orifice, thus preventing ingress of dirt, evaporation of the product, and atmospheric contamination.

In another embodiment of the invention, the liquid to be sprayed is caused to flow past a spherical surface and through a gap formed between that surface and a circumambient hole in a plate. The plate is preferably made of a spring material and located so that it is in sealing contact with the spherical surface as a normally closed valve. Under the action of liquid under pressure, the plate is forced away from the spherical surface by an amount determined by the stop, which may be fixed or adjustable, and the fluid flows through the gap thus formed to emerge as a thin circular sheet. As the sheet of liquid expands, it becomes thinner, and the outer edge breaks into droplets, the diameter of which are determined by the size of the gap, the pressure of liquid and the physical properties of the liquid. When the pressure in the liquid is reduced below a predetermined level, the spring plate returns to its original position to seal against the spherical surface, thus preventing ingress of dirt, evaporation of the remaining product, and atmospheric contamination.

Whilst reference has been made above to the use of a ball or spherical surface in co-operation with a circular orifice in a plate or nozzle, other shapes could be used, for example, a conical surface co-operating with a circular hole. The precise profile of the surface and hole will be determined in part by the spray pattern required, and the present invention provides for all combinations of surfaces and holes, but it is preferred that at least one of the components has a varying cross section so that the gap between them is opened or closed as a result of relative movement. Since the stop ensures that the gap is of substantially constant size when the components are fully apart, an even spray results from the passage of fluid throughout the length of the gap. The width of the gap is preferably of the order of 5 micrometers. The ratio of the length of the gap L to the width of the gap D is preferably not more than 1 and more preferably not more than 0.5. By the "length" of the gap we mean the distance which the liquid has to travel in order to pass through the gap.

The surface finish of the co-operating components in the region of the gap should be sufficiently fine so as not to adversely affect the droplet size and pattern of the spray: for example, a groove in one component would cause a stream of liquid to issue therefrom, which would probably not have the required characteristics, and could lower the pressure in the liquid sufficiently to adversely affect the quality of spray emerging from the remainder of the gap. The finish should be sufficiently fine to ensure efficient sealing between the components when in the closed position.

The invention further provides an atomizing device which comprises an atomizing nozzle according to the present invention, a supply of liquid, and means for providing liquid under pressure from said supply to said nozzle.

In one form, the device is an inhalation device, and the liquid comprises a medicament suitable for inhalation. The liquid may contain the medicament in suspension or solution, and the liquid may be an aqueous or non-aqueous liquid which is physiologically acceptable.

DETAILED DESCRIPTION OF PREFERRED EMBODIMENTS

Figure 1:
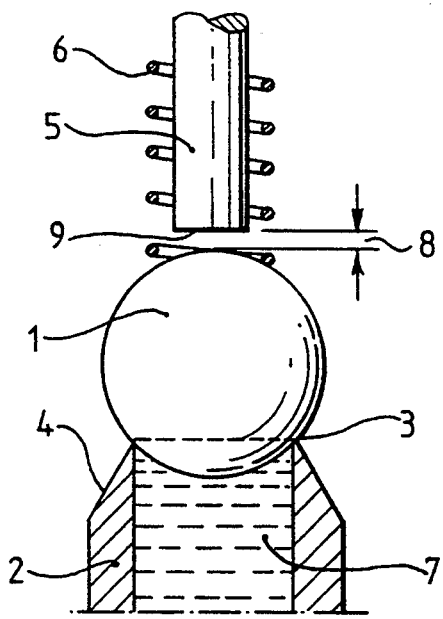
FIG. 1 illustrates the principle of the invention and is a cross sectional view of the basic elements in their normal, non-pressurised relationship.

Referring to FIG. 1, ball 1 is resiliently urged by a compression spring 6 into a position in which it is sealingly located on the circular orifice 3 of nozzle 2. Stop means 5 is located on the longitudinal axis of the ball and orifice, and has a gap 8 between the face 9 of the stop means 5 and the surface of ball 1. Nozzle 2 is in hydraulic communication with a dispensing means (not shown) and contains liquid 7 which is to be sprayed.

Figure 2:
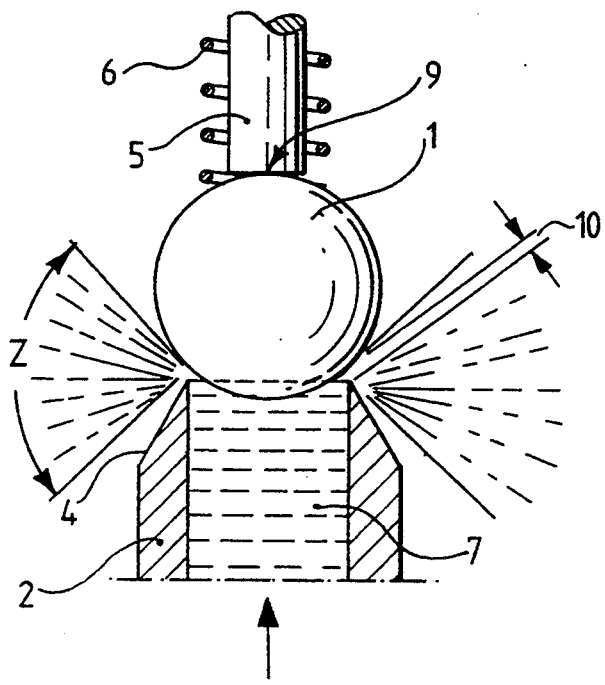
FIG. 2 is a similar view to FIG. 1, and shows the elements in the operating position.

Referring now to FIG. 2, which illustrates the same components as in FIG. 1, pressure has been applied to the liquid 7 by the dispensing means, and ball 1 is lifted from the circular orifice 3 against the force of spring 6 until it stops against the face 9 of stop means 5. Thus the ball 1 has moved by an amount controlled by the gap 8 to form a gap 10, the size of which is less than gap 8 by an amount determined by the ratio of the diameters of the ball 1 and circular orifice 3. The liquid 7 issues through the gap 10 as a circular sheet of thickness initially determined by the size of gap 10. As the liquid sheet expands it becomes thinner, until the surface tension of the liquid is unable to maintain homogeneity of the sheet, and the periphery of the sheet breaks into small droplets. The size of the droplets is controlled by the dimension of the gap 10 and the velocity of the liquid, which in turn depends on the pressure generated in the dispenser. A smaller gap 10 will generally produce smaller droplets, provided that the pressure in the liquid is sufficiently high to overcome the viscous drag created by the small gap, and accelerate the liquid to form a thin sheet. (If the pressure is too low, the liquid will merely ooze from the gap).

When the pressure in the liquid 7 ceases, the ball 1 is returned to sealing contact with orifice 3 by spring 6. It is preferable that the contact line between the ball 1 and orifice 3 is very thin, which may be facilitated by chamfering the nozzle as at 4, so as to leave a knife edge. This may have the additional effect of allowing a wider spray angle Z than possible with a square-edged orifice. The orifice 3 has a chamfered peripheral surface with the direction of chamfering being such as to reduce the length of the gap between the ball 1 (closure member) and the nozzle 2 (orifice-defining means).

Figure 3:
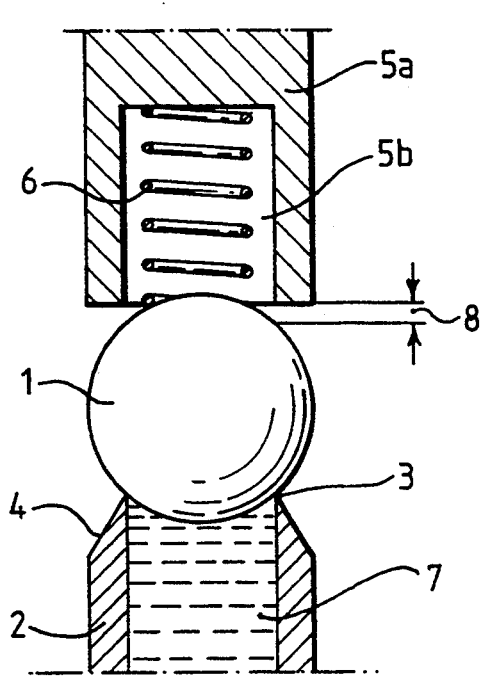
FIGS. 3 and 4 show a modified form of the embodiment of FIGS. 1 and 2.
Figure 4:
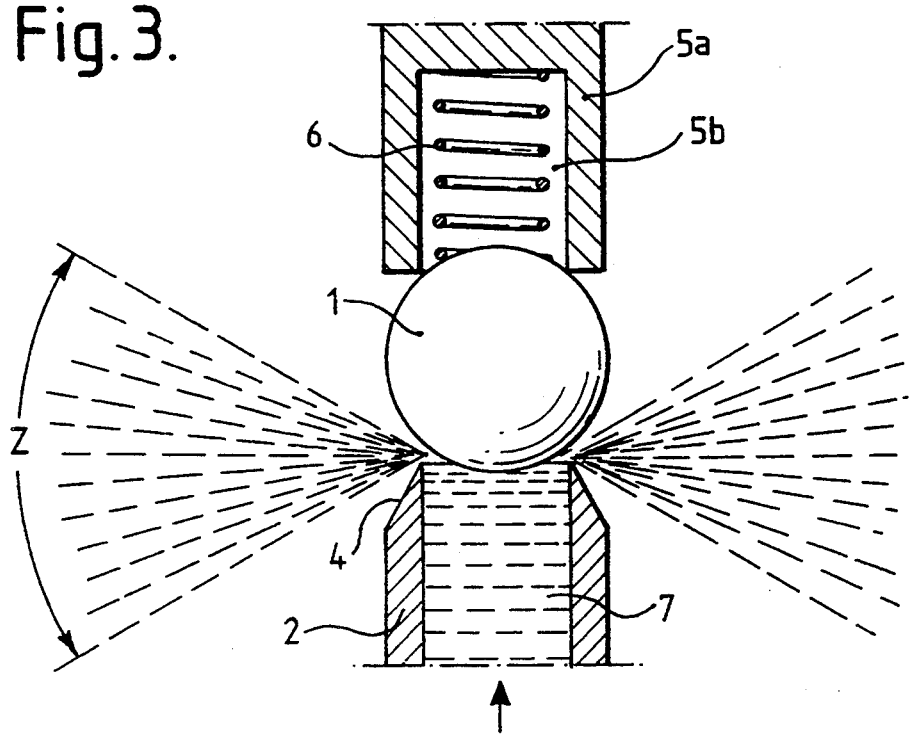

FIGS. 3 and 4 show a modification in which the stop means 5 is replaced by an alternative stop means 5a which has a recess 5b within which the spring 6 is housed. When the nozzle goes from the closed position shown in FIG. 3 to the open position shown in FIG. 4, the ball 1 seats itself in the open end of the recess. The guidance which this provides ensures that the ball is correctly aligned with respect to the end of the conduit 2, with a uniform annular gap between the orifice 3 and the ball. The spray produced is thus substantially uniform both in distribution around the gap and in droplet size.

Figure 5:
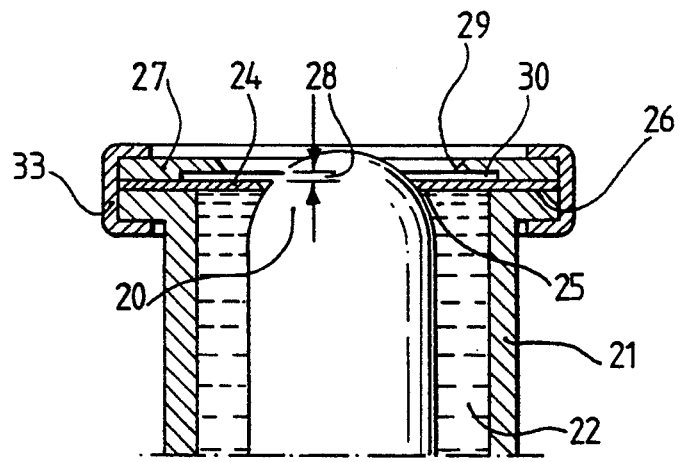
FIGS. 5 and 6 show an alternative embodiment of the principle of the invention, in closed and open position respectively.
Figure 6:
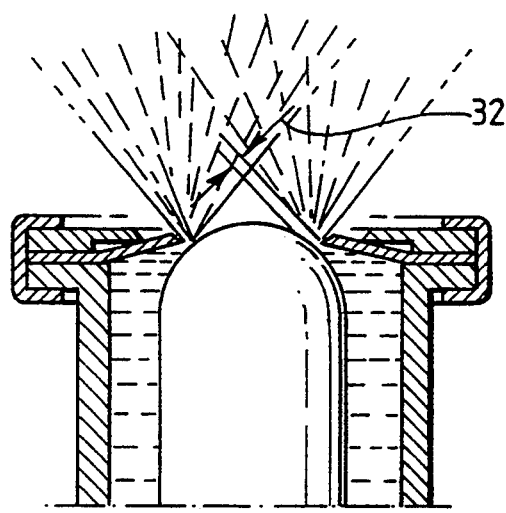
Figure 7:
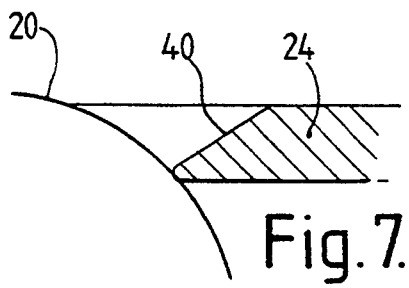
FIG. 7 is an enlarged part section showing the conjunction of the principal components illustrated in FIGS. 5 and 6.
Figure 8:
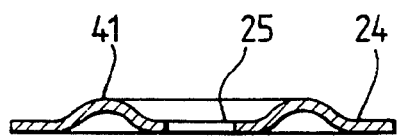
FIG. 8 shows a section through a modified version of the spring plate used in the embodiment FIGS. 5 and 6.
Figure 9:
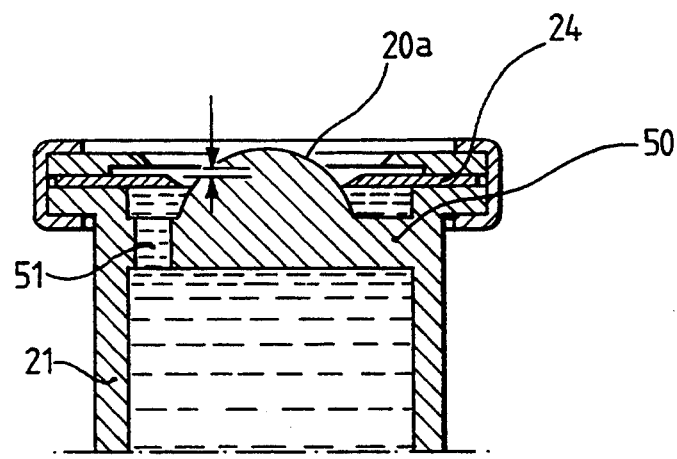
FIGS. 9 and 10 show a modified form of the embodiment of FIGS. 5 and 6.
Figure 10:
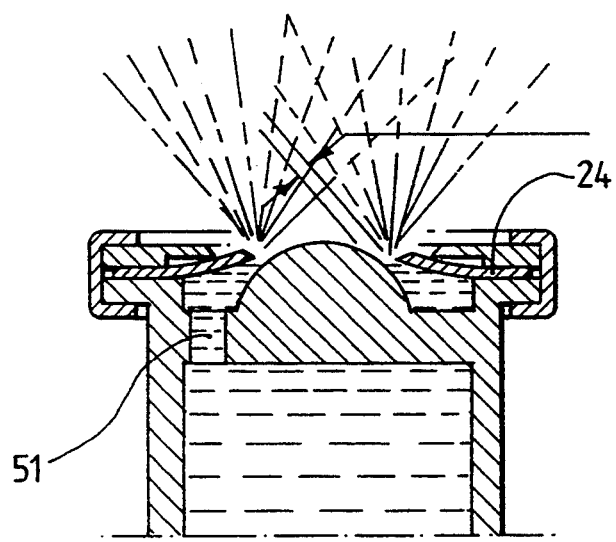
Figure 11:
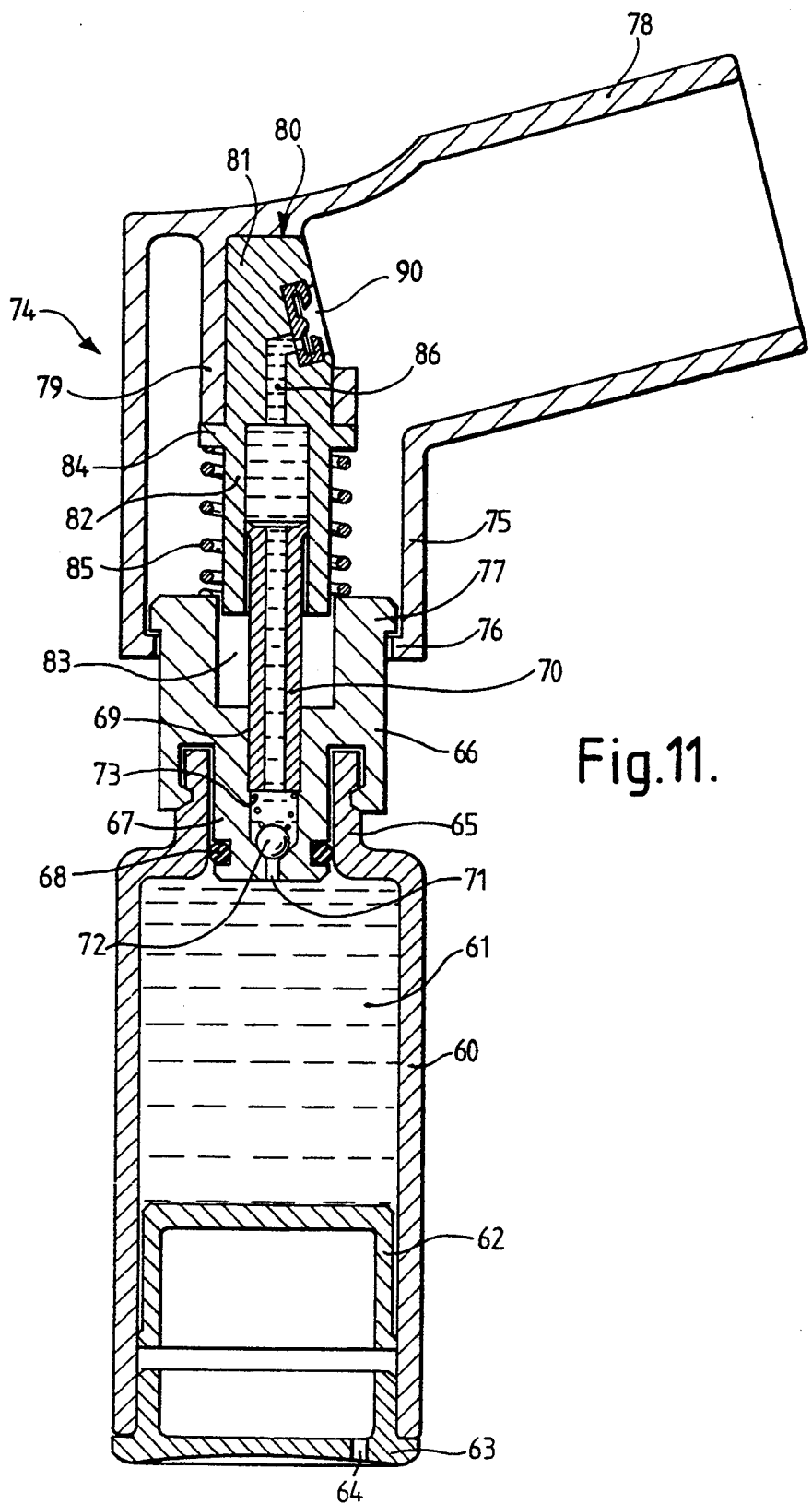
FIGS. 11 and 12 show a spray device for use as an inhaler, incorporating a nozzle according to the present invention.
Figure 12:
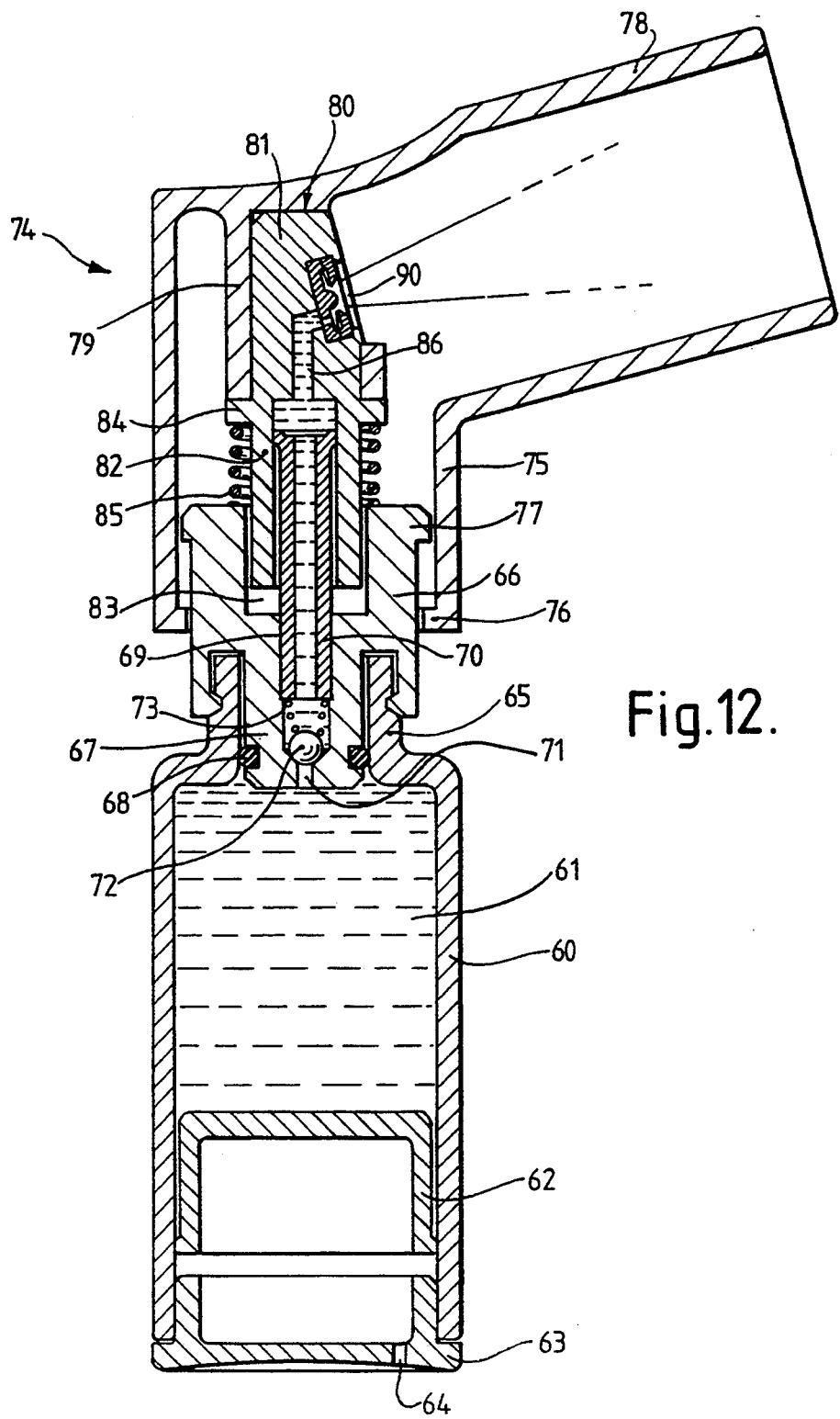
Figure 13:
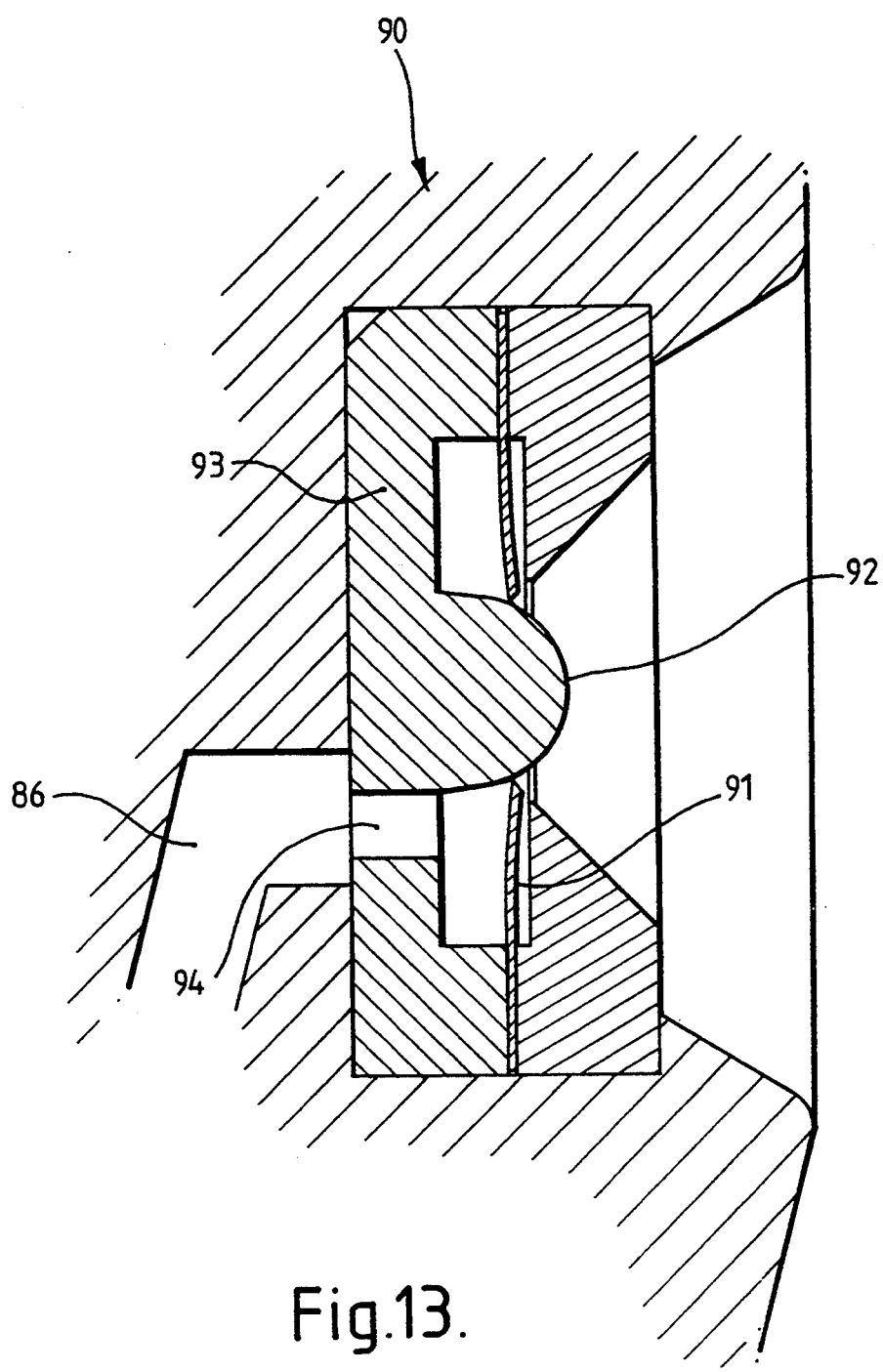
FIG. 13 shows the nozzle used in FIGS. 11 and 12, on a larger scale.

An alternative embodiment is shown in FIGS. 5 and 6. In this case, FIG. 5 shows a spherical surface 20 which is located at the outer edge of the discharge conduit 21 containing the liquid to be sprayed 22. A spring plate 24 having a circular orifice 25 is held against the spherical surface 20 so that the circular orifice 25 makes sealing contact with the spherical surface 20, and the outer edge of the spring plate 24 is in sealing contact with the abutment face 26 of conduit 21, thus preventing the passage of liquid 22. A plate 27 having a circular hole 29 is assembled on to the outer face of spring plate 24 so that the hole 29 is co-axial with orifice 25. A step or recess 30 in plate 27 provides a gap 28 between the spring plate 24 and plate 27, the assembly of the two plates being held in sealing contact with the abutment 26 by retaining member 33, which may be a crimped-on ring as shown.

Referring to FIG. 6, the liquid 22 is pressurised by the dispensing means (not shown), and forces plate 24 away from the spherical surface 20, against the inherent bias provided by the fact that the plate 24 is a spring plate, to create the gap 32 between the circular orifice 25 and spherical surface 20. The size of the gap 32 is determined by the size of the gap 28 and by the diameter of the hole 29 in the plate 27, which, between them, determine the extent to which the spring plate 24 can flex. The liquid issues from the gap 32 as a thin circular sheet, the outer edge of which breaks into droplets as previously described. The edge of the circular orifice 25 in spring plate 24 may have a chamfer 40 as shown in FIG. 7, which may permit a wider spray angle than possible with a square-edged orifice. The spring plate 24 may have corrugations 41 co-axial with the orifice 25 as shown in FIG. 8, which will facilitate the flexing of the spring plate. When the pressure is removed from the liquid 22, the spring plate 24 returns to sealing contact with the spherical surface 20.

In FIGS. 5 and 6 the spherical surface 20 is shown diagrammatically as being at the end of a rod, and means (not shown) would be required to support the rod with respect to the fluid discharge conduit 21.

FIGS. 9 and 10 show a modified embodiment in which there is a spherical surface 20*a* formed on a disc 50 which is secured to, or integral with, the inner wall of the conduit 21. The disc 50 is provided with at least one port 51 through which liquid can pass from the interior of the conduit 21 to the region immediately below the plate 24.

FIGS. 11 to 13 show a spray device incorporating an atomizing nozzle according to the present invention. It is intended for use as an inhalation device. It comprises a reservoir 60 of liquid 61. The liquid 61 may, for example, consist of an aqueous suspension of a medicament suitable for treatment of a condition such as asthma. The lower end of the reservoir is defined by a piston 62 which is longitudinally slidable within the reservoir. Beneath the piston is a stopper 63 which has at least one orifice 64 therein to permit air to enter the space beneath the piston.

The upper end of the reservoir has a neck portion 65 to which a closure member 66 is secured. A portion 67 of the closure member extends within the neck, and an O-ring seal 68 provides a seal between the neck portion 65 and the portion 67. The closure member 66 has a passage 69 therethrough and a tube 70 is secured in the upper portion of this passage. The lower portion of the passage defines an orifice 71, above which is a tapered portion defining a seat for a check valve ball 72. The ball is urged against the seat by a compression spring 73.

An outlet member 74 is mounted on the closure member 66 so as to be movable with respect thereto. The outlet member 74 comprises a generally cylindrical part 75 the lower end of which engages over the closure member 66. The part 75 is prevented from separating from the closure member 66 by interengaging flanges 76 and 77 thereon. The outlet member 74 further comprises an outlet spout 78 through which a user can inhale through his or her mouth. In the case of an inhaler for nasal use, the spout 78 would be replaced by an appropriate nasal outlet.

In the region of the junction between the cylindrical part 75 and the outlet 78, the outlet member 74 has an inwardly extending wall 79 which serves to retain an atomizing arrangement 80. This includes a block 81 which has a hollow lower portion 82 which surrounds the upper end of the tube 70 and which is free to enter a cavity 83 in the upper end of the closure member 66. The hollow portion 82 has an outwardly extending flange 84 at its upper end, and a compression spring 85 is mounted between the flange and the closure member 66.

The interior of the hollow portion 82 communicates via a passage 86 with an atomizing nozzle 90 according to the invention. This is shown on a larger scale in FIG. 13. As can be seen there, it corresponds substantially to what is shown in FIGS. 9 and 10, and comprises a spring plate 91 which cooperates with a spherical surface 92 formed on a disc 93. The disc 93 is provided with at least one port 94 therethrough.

In operation, the user places his or her mouth over the spout 78 and squeezes the reservoir 60 and outlet member 74 together against the force of the compression spring 85 to bring the device into the position shown in FIG. 12. During this operation, the ball 72 prevents liquid leaving the reservoir 60 through the orifice 71, and the tube 70 acts as a piston to expel part of the liquid above the ball through the nozzle 90 where it forms an atomized spray. The quantity of liquid expelled in this way constitutes a metered dose, metering being effected by the stroke of the piston. The user inhales this spray. When the user ceases to hold the reservoir 60 and outlet member 74 together, the spring 85 forces them apart. This creates a suction effect within the tube 70 which draws the ball 72 away from its seat and permits liquid to pass from the reservoir through the orifice 71 to replenish what has just been dispensed through the nozzle 90. As the volume of liquid within the reservoir is reduced, the piston 62 slides upwardly under the force of the atmospheric pressure below it, air reaching the underside of the piston through the port 64.

Figure 14:
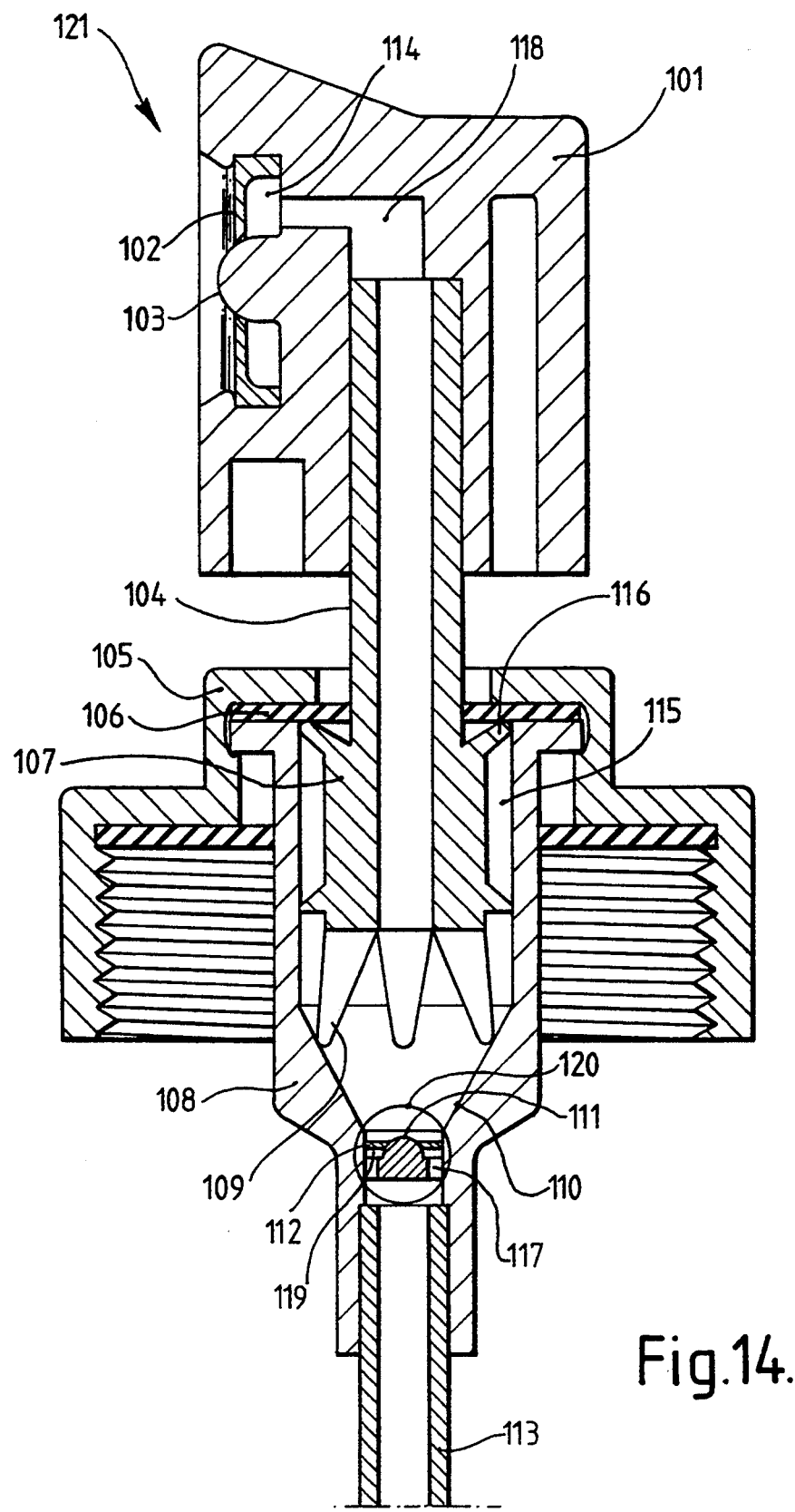
FIG. 14 shows another form of spray device incorporating the nozzle according to the invention.

FIG. 14, shows another embodiment of spray device. The figure shows the device in the discharge position. In this embodiment, a valve of similar design to that used as the atomizing nozzle is used also as a non-return inlet valve. FIG. 14 shows an actuator 101 sealingly located on a hollow stem 104 which is integral with a hollow piston 107. Piston 107 is slidingly located within the cylinder 115, the cylinder being formed as the inner part of a pump body 108. The body is retained by a snap fit or other convenient method of retention in a closure 105, a gasket 106 providing a seal between the stem 104 and the closure 105. Gasket 106 is free to flex with axial displacement of the piston and stem, whilst maintaining a seal. A plurality of cantilever springs 109, formed integrally with piston 107, urges the piston in an outward direction by reacting against a conical surface 110 formed in the lower part of the pump body 108. The piston is prevented from coming out of the pump body 108 by an abutment 116 closing on to the gasket 106 which is supported by the inside of the closure 105.

The lower end of the pump body 108 contains a spherical surface 111. A flexible diaphragm 112 with a circular hole therein is sealingly located in the pump body 108 so that the edge of the hole is in sealing engagement with the spherical surface 111. The combination of diaphragm 112 and surface 111 acts as a normally closed non-return valve 120. The extreme lower part of the pump body 108 terminates in a diameter adapted to sealingly retain a dip tube 113. The conduit defined by the dip tube 113 and extreme lower part of the pump body 108 is in communication with an annulus 119 formed between the spherical surface 111 and the diaphragm 112 via one or more ports 117. The actuator 101 has a spherical surface 103, and a flexible diaphragm 102 with a circular hole therein, the edge of which hole is in sealing engagement with the spherical surface 103. The diaphragm 102 is sealingly located by a snap fit or other convenient method within the actuator 101, and the combination of diaphragm 102 and surface 103 acts as a combined non-return valve and atomizing nozzle 121. The hollow stem 104 is in communication with annulus 114 via a port 118.

In operation, the actuator is depressed and allowed to return several times to prime the pump, the valves 120 and 121 cooperating to draw liquid from a reservoir (not shown) and to discharge the liquid from the atomizing nozzle.

Figure 15:
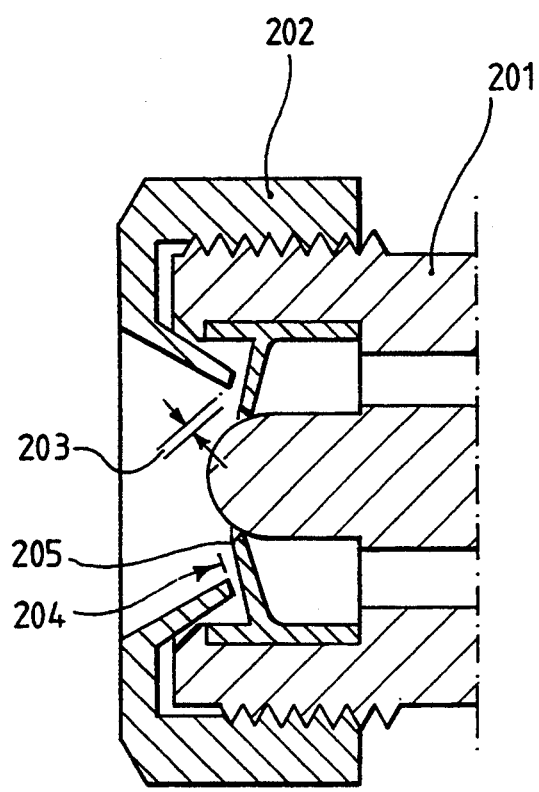
FIG. 15 shows an embodiment of the nozzle having a gap of adjustable size.

FIG. 15 shows an atomizing nozzle in which, unlike those described so far, a means is provided for enabling the gap through which the liquid passes to be adjusted. The nozzle comprises a body 201 which has a threaded exterior to receive a threaded cap 202. The cap may be adjusted to alter a gap 203 formed between a face 204 of the cap and a flexible diaphragm 205. In this way the discharge characteristics may be readily adjusted; for example a spray may be adjusted from a fine to a coarse droplet size.

Figure 16:
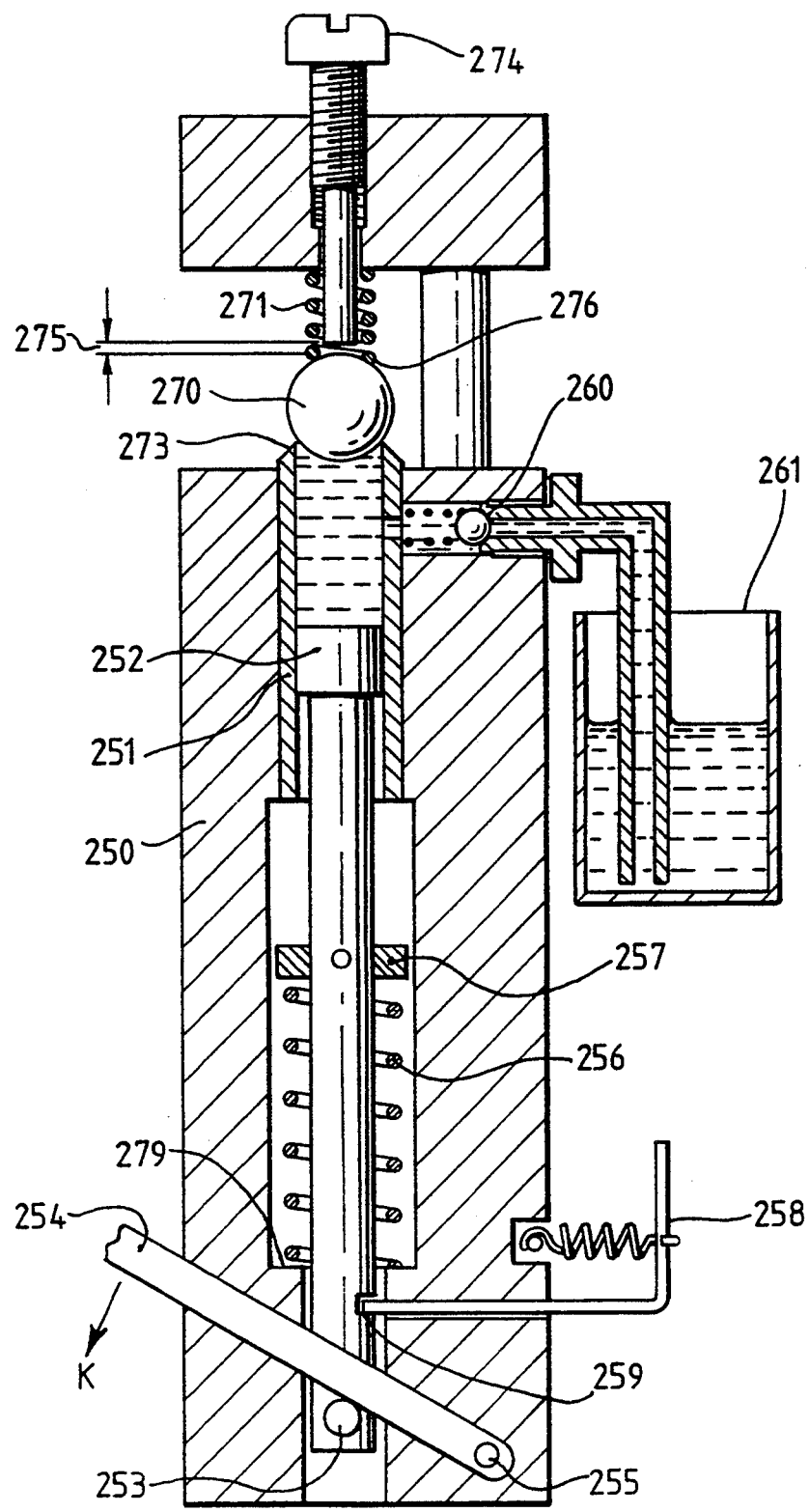
FIG. 16 shows another form of spray device incorporation the nozzle according to the invention.

A further embodiment of atomising device is shown diagrammatically in section in FIG. 16. Body 250 contains a cylinder 251, the upper end of which terminates in an orifice 273 sealed by a ball 270 urged by a compression spring 271. A piston 252 is sealingly and slidingly located in the cylinder 251. The lower end of piston 252 has a pin 253 on which a lever 254 acts. Lever 254 is pivoted on a pin 255. An abutment 279 supports a compression spring 256 which urges against a collar 257 attached to piston 252. Thus when lever 254 is operated in the direction of arrow K, the piston 252 is retracted in cylinder 251 against the load of spring 256. The depression thus created in the cylinder between the piston 252 and ball 270 causes liquid from a reservoir 261 to flow into the cylinder via a non-return valve 260. At a predetermined point, a latch mechanism 258 engages with a detent 259 to hold the piston 252. When the latch 258 is pulled out of engagement with the detent 259 the spring 256 causes the piston to suddenly pressurise the liquid. The pressure is sufficient to overcome the loading of spring 271 on ball 270, which lifts off an orifice 273 to permit the passage of liquid through a gap thus formed between the orifice 273 and ball 270. A spray is then created in the manner described above. A finely threaded screw 274 may be operated to adjust the gap 275 between the end face 276 of the screw 274 and the top surface of ball 270. Thus the amount that the ball 270 lifts away from orifice 273, and hence gap, may be adjusted to change the droplet size contained in the spray.

The description "liquid" used in this specification includes solutions, suspensions and emulsions.

I claim:

1. An atomizing device for producing a spray of droplets from a liquid passing through the nozzle under pressure, which nozzle comprises means defining an orifice; a closure member for the orifice, the orifice-defining means and closure member being relatively movable with respect to one another between a first position in which the closure member cooperates with the orifice to close the orifice and a second position in which the closure member is spaced from the orifice-defining means to define a gap therebetween, said orifice-defining means being a flexible diaphragm provided with at least one corrugation surrounding the orifice, whereby to increase the flexibility of the diaphragm; and a stop for limiting relative movement between the orifice-defining means and the closure member to ensure that a width of the gap cannot exceed that which would produce a fine spray, the device further comprising a supply of the liquid, and means for providing the liquid under pressure from said supply to said nozzle.

2. A device according to claim 1, wherein the orifice is circular.

3. A device according to claim 2, wherein the closure member has an at least partly spherical surface positioned to cooperate with the orifice.

4. A device according to claim 1, wherein the closure member is a spherical ball.

5. A device according to claim 1, wherein the orifice-defining means and the closure member are relatively movable with respect to one another under a force exerted by pressure of the liquid.

6. A device according to claim 1, wherein the orifice defining means has a chamfered peripheral surface, the direction of chamfering being such as to reduce the length of the said gap.

7. A device according to claim 1, wherein the width of said gap is of the order of 5 micrometers.

8. A device according to claim 1, wherein the value of L/D, where L is the length of the said gap and D is the width of said gap, is not more than 1.

9. A device according to claim 8, wherein the value of L/D is not more than 0.5.

10. A device according to claim 1, wherein the orifice-defining means and the closure member are biassed to the said first position.

11. A device according to claim 10, wherein said bias is a resilient bias.

12. A device according to claim 11, wherein said resilient bias is provided by the orifice-defining means being resiliently movable.

13. A device according to claim 12, wherein said liquid comprises a medicament suitable for inhalation.

14. A device according to claim 13, wherein said liquid contains the said medicament in suspension.

15. A device according to claim 14, wherein said liquid contains said medicament in solution.

16. A device according to claim 13, wherein said liquid is a physiologically acceptable aqueous liquid.

17. A device according to claim 13, wherein said liquid is a physiologically acceptable non-aqueous liquid.

18. A device according to claim 1, comprising metering means for ensuring that said liquid passes through said nozzle in metered quantities.

19. A device according to claim 1, wherein said stop is configured to engage said closure men%her to ensure that said gap is uniform and that the fine spray produced is substantially uniform in distribution around said gap and in droplet size.

20. A device according to claim 1, wherein said stop is arranged and configured to define an extent to which said flexible diaphragm may flex so that an outer edge of a sheet of liquid emerging from said gap breaks into droplets.

21. A device according to claim 1, wherein said stop is arranged for engaging said closure member to effect the limiting of relative movement between the orifice-defining means and the closure member, said orifice-defining means, said closure member and said stop being configured and arranged relative to each other to ensure that said closure member is aligned with said orifice during engagement of said stop with said closure member so that said gap between said orifice-defining means and said closure member is uniform and annular.

22. An atomizing device for producing a spray of droplets from a liquid passing through the nozzle under pressure, which nozzle comprises means defining an orifice; a closure member for the orifice, the orifice-defining means and closure member being relatively moveable with respect to one another between a first position in which the closure member cooperates with the orifice to close the orifice and a second position in which the closure member is spaced from the orifice-defining means to define a gap therebetween, said orifice-defining means being a flexible diaphragm; and a stop for limiting relative movement between the orifice-defining means and the closure member to ensure that a width of the gap cannot exceed that which would produce a fine spray, the stop comprising an annular ring having a stop surface located adjacent to, but spaced from, the diaphragm, the device further comprising a supply of the liquid, and means for providing the liquid under pressure from said supply to said nozzle.

23. A device according to claim 22, comprising metering means for ensuring that said liquid passes through said nozzle in metered quantities.

24. A device according to claim 22, wherein said liquid comprises a medicament suitable for inhalation.

25. A device according to claim 24, wherein said liquid contains said medicament in suspension.

26. A device according to claim 25, wherein said liquid contains said medicament in solution.

27. A device according to claim 24, wherein said liquid physiologically acceptable aqueous liquid.

28. A device according to claim 24, wherein said liquid is a physiologically acceptable non-aqueous liquid.

* * * * *